United States Patent [19]

Larnard et al.

[11] Patent Number: 5,086,772
[45] Date of Patent: Feb. 11, 1992

[54] ARRHYTHMIA CONTROL SYSTEM EMPLOYING ARRHYTHMIA RECOGNITION ALGORITHM

[75] Inventors: Donald J. Larnard, Davie; Andre G. Routh, West Melbourne, both of Fla.

[73] Assignee: Telectronics Pacing Systems, Inc., Englewood, Colo.

[21] Appl. No.: 559,295

[22] Filed: Jul. 30, 1990

[51] Int. Cl.$^5$ ............................................. A61N 1/39
[52] U.S. Cl. ............................ 128/419 D; 128/419 PG
[58] Field of Search ............ 128/419 D, 419 PG, 205, 128/206

[56] References Cited

U.S. PATENT DOCUMENTS

| | | | |
|---|---|---|---|
| 3,857,398 | 12/1974 | Rubin | 128/419 D |
| 4,296,755 | 10/1981 | Judell | 128/419 D |
| 4,523,595 | 6/1985 | Zibell | 128/419 D |
| 4,552,154 | 11/1985 | Hartlaub | 128/419 PG |
| 4,587,970 | 5/1986 | Holley et al. | 128/419 PG |
| 4,614,192 | 9/1986 | Imran et al. | 128/419 D |
| 4,796,620 | 1/1989 | Imran | 128/706 |
| 4,869,252 | 9/1989 | Gilli | 128/419 PG |
| 4,895,151 | 1/1990 | Grevis et al. | 128/419 PG |
| 4,940,054 | 7/1990 | Grevis et al. | 128/419 PG |
| 4,971,058 | 11/1990 | Pless et al. | 128/419 D |
| 4,974,601 | 12/1990 | Tranjan et al. | 128/706 |

FOREIGN PATENT DOCUMENTS

| | | | |
|---|---|---|---|
| 0023134 | 1/1981 | European Pat. Off. | 128/706 |
| 2544989 | 11/1984 | France | 128/705 |

Primary Examiner—William E. Kamm
Attorney, Agent, or Firm—Gottlieb, Rackman, & Reisman

[57] ABSTRACT

An arrhythmia control method and device are disclosed which monitor the cardiac state of a patient, utilize an arrhythmia recognition algorithm to detect and distinguish among bradycardia, sinus rhythm, supraventricular tachycardia and ventricular fibrillation, and deliver therapy in the form of electrical energy to cardiac tissue to revert selected arrhythmias and restore normal sinus rhythm. In its preferred form the device is an implantable combined dual chamber pacing and cardioverting device that is adapted to be electrically connected to the atrium and ventricle for sensing the atrial and ventricular waveforms and deliverying shock therapy thereto as required. The arrhythmia recognition algorithm utilizes the sensed atrial and ventricular waveform data for, among other things, distinguishing between ventricular tachycardia and supraventricular tachycardia.

31 Claims, 7 Drawing Sheets

EVENT CLASSIFICATION

FIG. 7

ARRHYTHMIA CONTROL SYSTEM EMPLOYING ARRHYTHMIA RECOGNITION ALGORITHM

TECHNICAL FIELD

This invention relates to an arrhythmia control method and device which monitors the cardiac state of a patient, utilizes an arrhythmia recognition algorithm to detect and distinguish among bradycardia, sinus rhythm, supraventricular tachycardia, ventricular tachycardia and ventricular fibrillation, and delivers therapy in the form of electrical energy to cardiac tissue to revert selected arrhythmias and restore normal sinus rhythm.

As used herein, antitachycardia pacing refers to any pacing for the reversion of tachycardia. The term tachyarrhythmia refers to any fast abnormal rhythm of the heart which may be amenable to treatment by electrical discharges. This specifically includes ventricular tachycardia (VT), supraventricular tachycardia (SVT), ventricular flutter and ventricular fibrillation (VF), atrial tachycardia (AT), and atrial flutter and atrial fibrillation (AF).

The term therapy as used herein includes the processes used between the detection and the reversion of an arrhythmia and includes the actions of bradycardia pacing, antitachycardia pacing, cardioversion and/or defibrillation shocks. The term cardioversion refers to the discharge of electrical energy into the cardiac tissue in an attempt to terminate or revert an arrhythmia. This may take the form of a high energy discharge (up to 40 Joules or more) or a low energy discharge (less than 1 Joule). The discharge may be monophasic or biphasic but is ntt restricted to these waveforms. Cardioversion shocks may or may not be synchronized to the rhythm of the heart. Defibrillation is a particular example of cardioversion.

This invention applies equally to devices which deliver energy synchronized to an R-wave and to those that do not, and it applies to devices which use lower energy pulses as well as to devices which use higher energy pulses. The invention applies to devices which deliver cardioverting shocks alone, as well as to devices which deliver cardioverting shocks in combination with bradycardia or antitachycardia pacing pulses. The invention will usually apply to implantable multiple chamber cardioverters or defibrillators, but is also applicable in one form to single chamber implantable ventricular or atrial cardioverters and to external cardioverters.

BACKGROUND ART

U.S. Pat. No. 3,857,398 to Rubin, entitled "Electrical Cardiac Defibrillator", describes a combined cardiac pacer and defibrillator device which performs a pacing or a defibrillating function depending on the condition detected. When the device detects tachycardia, it switches to a defibrillating mode and, after a period of time during which a charge is accumulated, delivers a defibrillation shock to the patient. When the device detects that the heart rate has fallen below a predetermined value, the pacer switches to a demand pacing mode and delivers pacing pulses to the heart.

A multiprogrammable, telemetric, implantable defibrillator is disclosed in the copending U.S. patent application Ser. No. 576,178 of Norma Louise Gilli et al., filed AUG. 29, 1990, entitled "Reconfirmation Prior To Shock In Implantable Defibrillator". This device contains a bradycardia support system as well as a high energy shock system to revert ventricular tachycardia to normal sinus rhythm. After reconfirmation of the presence of a tachycardia, high energy shock is delivered to the patient either at a predetermined time or when the desired energy level is reached.

Although technological improvements in implantable arrhythmia control devices have been made, a number of problem areas remain. Significant among these is the false triggering of electrical discharges in some instances of benign supraventricular tachycardia, for example sinus tachycardia with aberrant conduction. Such unnecessary discharges result in discomfort and potential danger to the patient.

DISCLOSURE OF THE INVENTION

It is therefore a primary object of this invention to incorporate in an arrhythmia control system provision for significantly reducing or eliminating the false triggering of electrical discharges due to the occurrence of benign supraventricular tachycardia in a patient.

According to the invention, there is provided an implantable combined dual chamber pacing and cardioverting device for the reversion of tachycardia, including means for sensing the atrial and ventricular waveforms of the heart, means for storing data relating to such waveforms, and means for delivering cardioversion shock therapy to the heart. The device further includes: means for detecting event peaks in the ventricular waveform and establishing event data windows extending for predetermined time periods with respect to each of the event peaks; means for determining the morphology of the ventricular waveform based at least in part on data stored during the time periods of the event data windows; means for classifying each of the events based on such morphology and outputting in real time one or another of a plurality of different values corresponding to one or another of a plurality of different heart rate categories, including at least a normal rate, a tachycardia rate and a ventricular fibrillation rate; and means for summing the outputs of the event classification scheme for a predetermined number of events and outputting in real time one or another of a plurality of different rhythm signals based on such summing and corresponding at least to a non-pathological rhythm, a ventricular tachycardia rhythm and a ventricular fibrillation rhythm, for use in determining the mode of shock therapy to be delivered to the patient's heart.

The invention also provides a method of reverting tachycardia in the heart of a patient. The method includes sensing the ventricular waveform of the heart; storing data corresponding to the ventricular waveform; detecting event peaks in the ventricular waveform and establishing event data windows extending for predetermined time periods with respect to each of the event peaks; determining the morphology of the ventricular waveform based at least in part on data stored during the time periods of the event data windows; classifying each of the events based on such morphology and providing in real time a plurality of different rate signals corresponding to one or another of a plurality of different heart rate categories, including at least a normal rate, a tachycardia rate and a ventricular fibrillation rate; summing such rate signals during a predetermined number of events and providing in real time one or another of a plurality of different rhythm signals based on such summing and corresponding to at least a non-pathological rhythm, a ventricular tachycardia rhythm and a ventricular fibrillation rhythm; and, delivering appropriate electrical shock therapy to the heart, or no therapy, in accordance with such rhythm signals.

BRIEF DESCRIPTION OF THE DRAWINGS

Further objects, features and advantages of the invention will become apparent upon consideration of the following detailed description in conjunction with the drawings, in which.

BEST MODE FOR CARRYING OUT THE INVENTION

Figure 1:
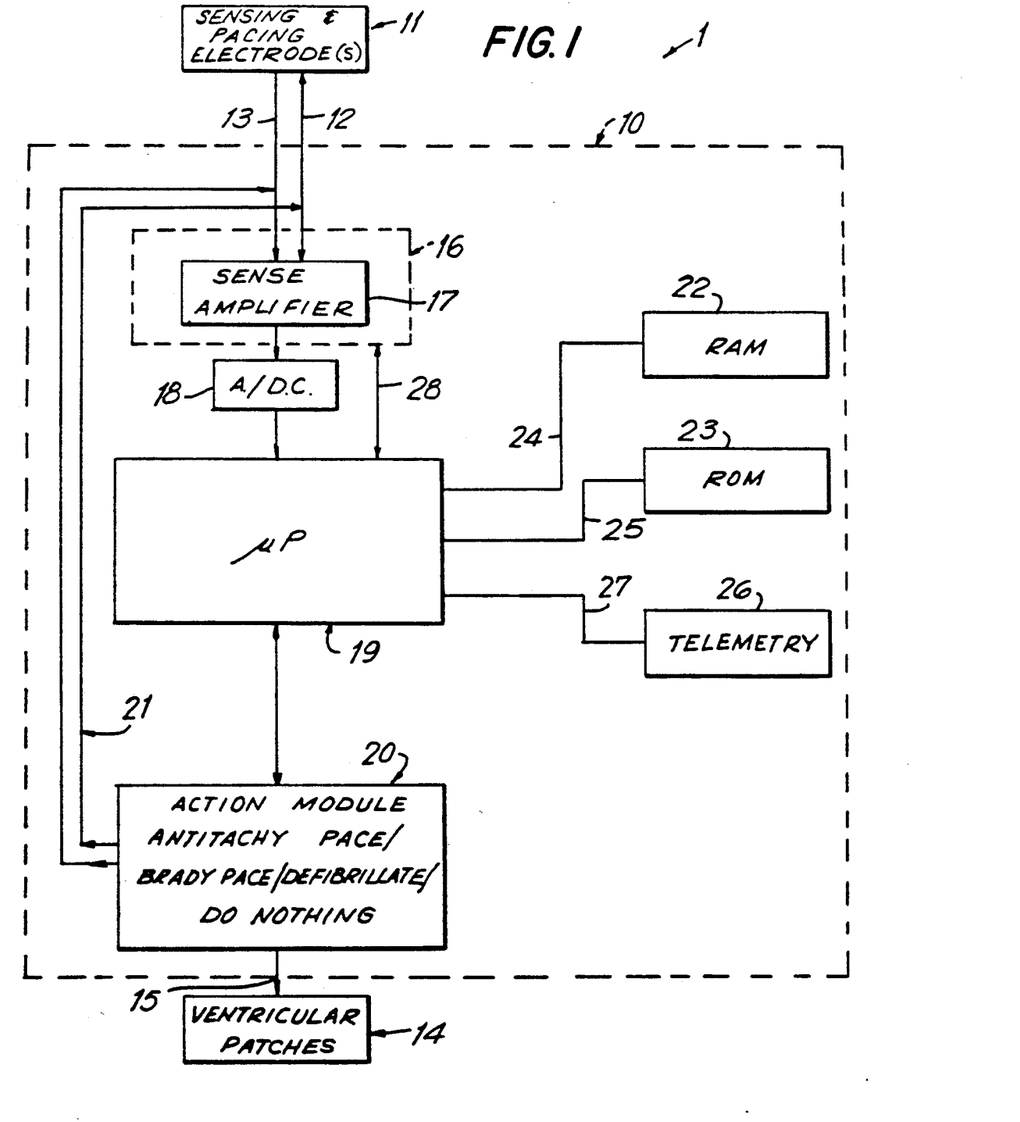
FIG. 1 is a block diagram of an arrhythmia control device in accordance with the present invention, which device may be either a single chamber or a dual chamber device.

Referring to FIG. 1, there is depicted a block diagram of an arrhythmia control device 1 which may be either a single chamber device or a dual chamber device. Device 1 is preferably designed to be implantable in a patient and includes a system module 10, one or more bipolar sensing and pacing electrodes, shown generally at 11, and appropriate leads 12 and 13 for connecting module 10 to the sensing electrodes 11. More particularly, when device 1 is a two chamber device, it will generally include an atrial sensing and pacing lead 12 extending to a corresponding one of the sensing and pacing electrodes 11 at the atrium of the patient's heart (not shown) for sensing atrial signals and administering pacing therapy to the atrium, and a ventricular sensing and pacing lead 13 extending to a corresponding one of the sensing and pacing electrodes at the ventricle of the patient's heart for sensing ventricular signals and administering pacing therapy to the ventricle. When device 1 is a single chamber device, the atrial sensing and pacing lead 12 and its associated sensing and pacing electrode are omitted from the device 1. In both cases the device 1 is further provided with one or more ventricular patches, shown generally at 14, for delivering defibrillation therapy to the ventricle of the heart, and suitable ventricular fibrillation leads 15 interconnecting the ventricular patches 14 and the system module 10. Endocardial defibrillator leads (not shown) may be used in place of the ventricular patches 14 and leads 15. In addition, a combination of endocardial lead(s) and epicardial patch(es) may be used.

An implantable dual chamber antitachycardia pacing, bradycardia pacing, defibrillating or cardioverting arrhythmia control device is disclosed in the copending U.S. patent application Ser. No. 462,499 of Norma Louise Gilli, filed Jan. 5, 1990, entitled "Apparatus and Method for Antitachycardia Pacing in Dual Chamber Arrhythmia Control System," now U.S. Pat. No. 4,998,974, dated Mar. 12, 1991, which is assigned to the assignee of the present invention and is incorporated herein by reference.

Device 1 is further provided with sensing circuitry, shown generally at 16, which includes an amplifier 17 for amplifying the cardiac signals sensed by electrodes 11. The amplified cardiac signals outputted by amplifier 17 are led to an analog-to-digital converter 18 which converts the cardiac signals to digital form and outputs the digital cardiac signals to a microprocessor, shown generally at 19, which, in response to various inputs received from other components of the module 10, performs various operations and generates various control and data outputs to an action module, shown generally at 20, which incorporates both pacemaking and defibrillating functions therein. Pacing therapy is delivered from the action module 20 to the atrial and ventricular sensing and pacing leads 11 and 12 by means of a bus, shown generally at 21. A suitable power supply (not shown), for example a battery in the case of an implantable device 1, is employed for the provision of reliable voltage levels to the various components of system module 10. A suitable end-of-life (EOL) signal line (not shown) is used to provide, to microprocessor 19, a logic signal indicative of the approach of battery failure in the power supply.

Microprocessor 19 is connected to a RAM unit 22 and to a ROM unit 23 by corresponding buses 24 and 25. Telemetry circuit 26, which is connected to microprocessor 19 by a bus 27, provides a bidirectional link between microprocessor 19 and an external device such as a programmer. It allows data such as the operating parameters to be read from or altered in the implanted system module 10.

As suggested in FIG. 1, action module 20 preferably includes circuitry for selectively providing one or another of antitachycardia pacing, bradycardia pacing, defibrillation therapy and no therapy, upon command from microprocessor 19. In addition when a two chamber device 1 is employed, the pacing therapy may be selectively provided to the atrium or ventricle, as called for by the microprocessor.

In operation, sensing electrodes 11 detect atrial and ventricular analog signals from the heart. These signals are led to the sensing circuitry 16 on respective leads 12 and 13. In addition, the sensing circuitry 16 receives input atrial and ventricular sense control signals from microprocessor 19, via bus 28, which determine the sensitivity applied to the detection circuit. As more fully described below, a change in this sensitivity will affect the voltage deviation required at the sensing electrode for a sense to be registered. A logic arrangement which may be used to control changes in the sensitivity is described in greater detail in the U.S. patent application Ser. No. 4,940,054 of Richard Grevis and Norma Louise Gilli, dated July 10, 1990 entitled "Apparatus And Method For Controlling Multiple Sensitivities In Arrhythmia Control System Including Post Therapy Pacing Delay," which description assigned to the assignee of the present invention and is incorporated herein by reference.

Atrial and ventricular pace control circuits (not shown) are provided in the action module 20 which cooperate with the microprocessor 19 to determine the respective types and magnitudes of atrial and ventricular pacing to occur. A logic arrangement which may be utilized to change the pulse energy is described in greater detail in the U.S. Pat. No. 4,869,252 of Norma Louise Gilli, entitled "Apparatus And Method For Controlling Pulse Energy In Antitachyarrhythmia And Bradycardia Pacing Devices," which description is incorporated herein by reference.

A suitable microprocessor 19 that may be used in connection with the present invention has been described in greater detail in the aforesaid U.S. Pat. No. 4,869,252 and is incorporated herein by reference. It comprises two 16-bit timers (not shown), a CPU (not shown), a vectored interrupts block (not shown), a ROM 23, a RAM 22, an external memory (not shown), ports (not shown) and an internal communications bus (not shown). RAM 22 acts as a scratch pad and active memory during execution of the various programs stored in ROM 23 and used by microprocessor 19. These programs include system supervisory programs, the arrhythmia recognition algorithm forming one of the main features of the present invention, to be described in greater detail hereinafter, and storage programs for storing, in external memory, data concerning the functioning of module 10 and the electrogram (EGM) provided by ventricular sensing and pacing lead 13. Signals received from telemetry circuit 26 permit an external programmer (not shown) to change the operating parameters of action module 20 by supplying appropriate signals to microprocessor 19.

Figure 2:
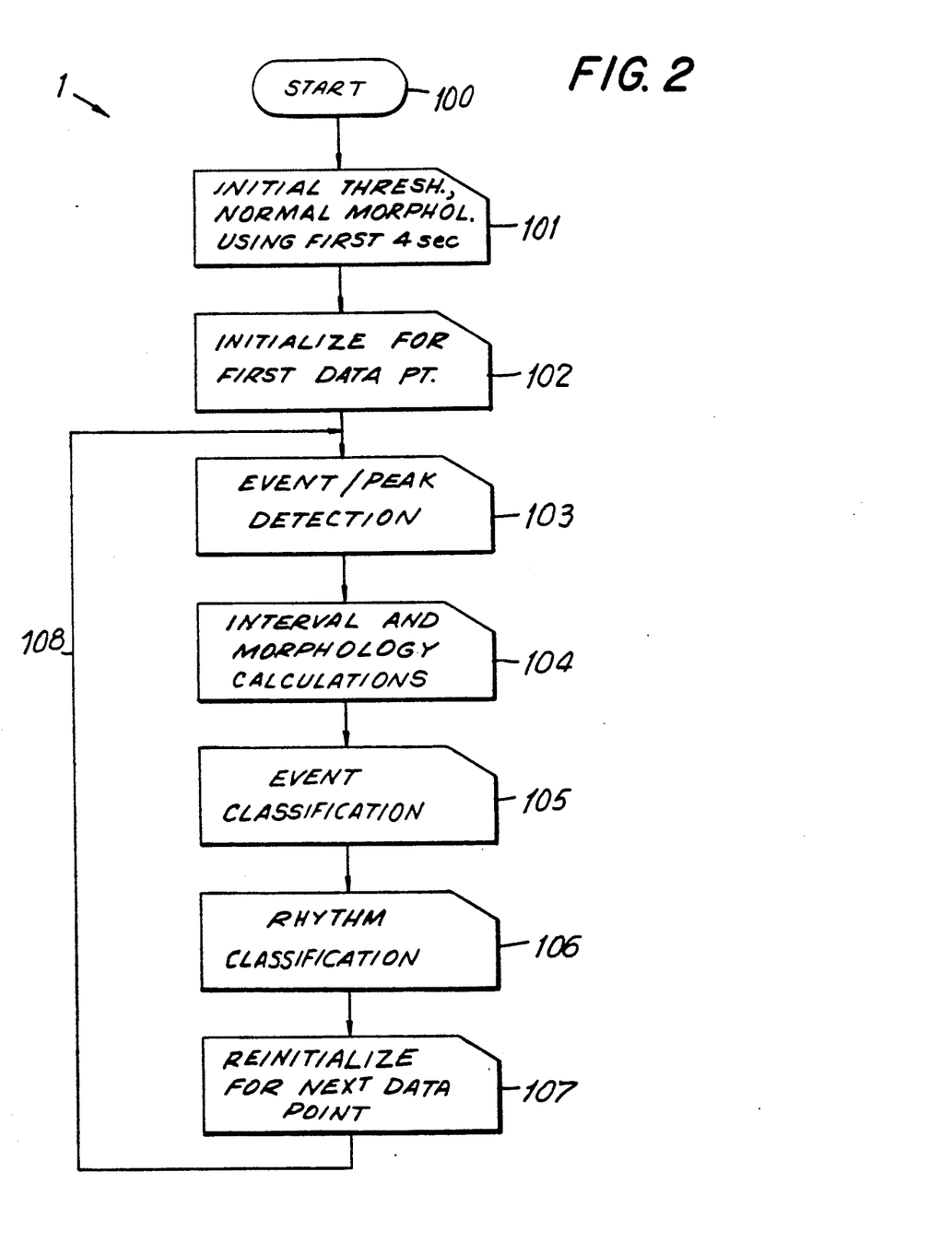
FIG. 2 is a generalized flow diagram of an arrhythmia recognition algorithm for the single chamber type of arrhythmia control device illustrated in FIG. 1.

Referring now to FIG. 2, a generalized flow diagram of an arrhythmia recognition algorithm for an implantable single chamber arrhythmia control device has there been illustrated. Although described herein in connection with a single chamber implantable arrhythmia control device, this algorithm may be used with externally located arrhythmia control devices which do not employ implanted sensing electrodes, and which apply high electrical energy defibrillation pulses to the external portion of a patient's chest. It is also applicable to externally located devices which are connected to electrodes implanted within the patient's chest.

Resuming consideration of FIG. 2, the starting point of the algorithm is shown at 100. Upon start-up of the device 1, the algorithm proceeds through a four second initialization step, shown at 101, during which normal sinus rhythm (NSR) data of the patient is analyzed to determine an event threshold level and to establish the morphology of an average normal sinus rhythm R-wave. The morphological features determined are the polarity of the R-wave and its duration or R-wave width. The algorithm is then initialized to start viewing data for rhythm analysis, as shown at 102. (The NSR event threshold level and morphology are periodically updated during operation of the device 1.)

At this point, the algorithm proceeds to its event and peak detection step or phase, shown at 103, wherein incoming electrogram (EGM) data analysis begins and event and peak detection of R-waves occur. Once the time of occurrence of the peak of the R-wave has been determined at 103, R-wave peak-to-peak interval calculations and R-wave morphology calculations are performed, at step 104.

The R-wave peak-to-peak interval and R-wave morphology calculation information developed at step 104 is then utilized in the event classification portion of the algorithm, at step 105. During event classification, each of the particular events are classified into one or another of the following four event classes: (i) a potential bradycardia event; (ii) a potential non-pathological event; (iii) a potential ventricular tachycardia (VT) event; and, (iv) a potential ventricular fibrillation (VF) event. In this classification scheme, if a potential supraventricular tachycardia (SVT) beat is resent, it is placed in the potential non-pathological event classification category. The foregoing event classification information is then utilized in the rhythm classification portion of the algorithm, at step 106.

During rhythm classification, the algorithm looks at, for example, the last eight event classifications and determines which particular rhythm is present. During rhythm classification, the current rhythm is updated after every new event, or after a predetermined asystole time setting is exceeded, indicating asystole is present.

Following the rhythm classification of data received at each data point, the algorithm reinitializes itself to receive data at the next data point, as shown at 107, and the flow diagram loops back at 108 to the event and peak detection step 103. The various detection, calculation and classification steps occurring between points 103 and 108 of the algorithm occur essentially in real time and data points are sampled at the clock rate of the microprocessor, so that substantially continuous data defining the patient's EGM is constantly being delivered to and processed by the algorithm in real time.

Figure 3:
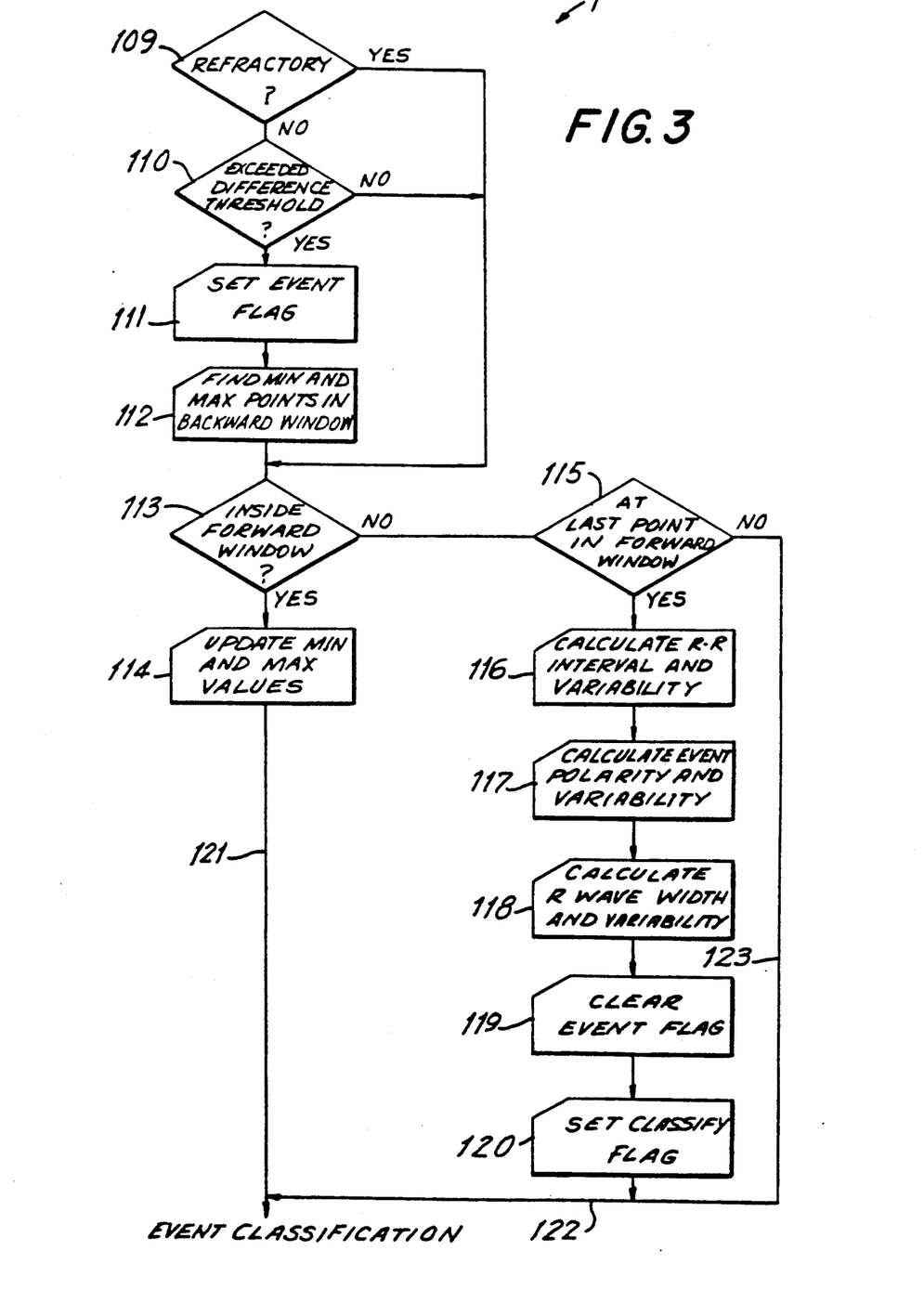
FIG. 3 is a logic flow diagram showing in greater detail a breakdown of those flow blocks of FIG. 2 that are labeled "EVENT/PEAK DETECTION" and "INTERVAL AND MORPHOLOGY CALCULATIONS"

Referring to FIG. 3 in conjunction with FIG. 2, a logic flow diagram is presented in FIG. 3 which shows in greater detail a breakdown of the flow blocks 103 and 104 of FIG. 2, relating respectively to the event and peak detection portion and to the interval and morphology calculation portion of the algorithm. As shown at 109, the first inquiry made by the algorithm after the initialization step at 102 is a determination of whether the algorithm is still in an "event data window" triggered by a previous event, which condition is termed a "refractory" condition, or whether sufficient time has passed since the last event occurred that the algorithm is no longer refractory.

As will appear in greater detail below, an event data window having a forward portion and a backward portion is established by the algorithm when an event peak that is greater than the threshold value by a predetermined amount is detected in the input EGM signal. The event data window extends for predetermined time periods before (backward window) and after (forward window) each such event peak. Preferably, the predetermined time period of the portion of the event data window occurring after such event peak (the forward window) is about fifty percent longer than the predetermined time period of the portion of the event data window occurring before such event peak (the backward window).

Assuming that the algorithm is not in refractory at 109, the algorithm checks each succeeding data point input for the onset of an R-wave event. The presence of an R-wave event is triggered when the EGM signal being input exceeds the specified threshold value by a "first difference threshold," as shown at 110. The specified threshold value is determined previously from the first four seconds of normal sinus rhythm data following the initial program start-up and initialization (i.e., at step 101 of FIG. 2). The first difference is directly proportional to the digital time derivative of the EGM signal. Thus, the event detector is triggered by exceeding a preset approximate first time derivative. The first order difference, D(k), for each time instance k, is defined as:

$$D(k) = x(k) - x(k-2) \quad (1.1)$$

where k = 2, 3, ..., and x is the input EGM signal. This type of difference is actually called a threepoint difference, since three sequential input EGM data points are required for its calculation.

Once an event is detected, the peak of the R-wave is determined with a search algorithm. An event flag is then set, as shown at 111, and an event data window is established, starting from a set number of data points backward in time from the flag, or trigger point, to a set number of data points forward in time of the trigger point (termed the backward and forward event data windows, respectively). The minimum and maximum amplitude values are found in the backward event data window, as shown at 112. The maximum amplitude, or peak value, $P_{peak}$, is defined as the amplitude with the largest absolute value:

$$P_{peak} = [x(K)]_{max} \quad (1.2)$$

where k ranges over the time period of the event data window. Similar considerations apply to establishing the minimum amplitude value.

After the minimum and maximum values have been established for the backward event data window at point 112 or, in those cases where the algorithm inquiry at point 109 shows a refractory condition or where there has been no signal input data that exceeds the threshold value at point 110, the algorithm inquires as to whether it is inside of, but not yet at the last data point in, the forward window of an event, as shown at 113. If such is the case, it continues to update the minimum and maximum values of the incoming EGM signal data, as shown at 114, sending these values to the event classification section of the device via line 121.

When the algorithm reaches the last data point of the forward window, as shown at 115, it performs a number of calculations on the data that has been stored. Thus, as shown at 116, the elapsed time between the event peak of the current event data window and the event peak of the last previous event data window is used for the calculation of the R-R (R-wave to R-wave) interval, RR(j), where j refers to the event number (first event is event number 1, second event is event number 2, etc.). The variability of each R-R interval is also calculated. This variability is not a true running variance computation, which requires considerable computation, but is known as a mean absolute deviation (MAD). The MAD calculation is a two-step process. First, a running mean, RR_ave(j), is calculated:

$$RR\_ave(j) = \left[ \sum_{m=1}^{m=8} RR(m) \right] / 8 \quad (1.3)$$

The MAD value, $RR_{mad}$, is calculated by averaging the absolute deviations of the eight most recent R-R values from the RR_ave:

$$RR_{mad}(j) = \left[ \sum_{m=1}^{m=8} [(RR(m) - RR\_ave(j))] \right] / 8 \quad (1.4)$$

This calculation is much simpler than the variance, and still provides a useable measure of the R-R variability.

The event polarity and variability are then calculated, as indicated at 117. The event polarity is established as a +1 if the peak amplitude is above the signal baseline or as a -1 if the peak amplitude is below the signal baseline. The event polarity MAD value is also calculated using equations 1.3 and 1.4, above, with the variable of event polarity being used, rather than R-R interval.

The R-wave width is then calculated, as indicated at 118, by finding the nearest points from the peak on either side of the peak which are ¼ the amplitude of the peak (baseline is considered to be equal to zero). This is not a direct measure of the R-wave width, but is a representative proportional measure of that value. The event R-wave width MAD value is then calculated using equations 1.3 and 1.4, with the R-wave width as the variable.

Upon completion of the foregoing calculations, which occur substantially in real time, a flag is set which signifies that the event has been completed and has been cleared from the event peak detection and the interval and morphology calculations portions of the device, as shown at 119. In addition a second flag is set which signifies that the event can now be classified, as shown at 120, and the algorithm advances to its event classification section, as shown by line 122. Also, when the algorithm proceeds beyond the last point in the forward window, at block 115, it advances to the event classification section of the algorithm, as shown by line 123.

Figure 4:
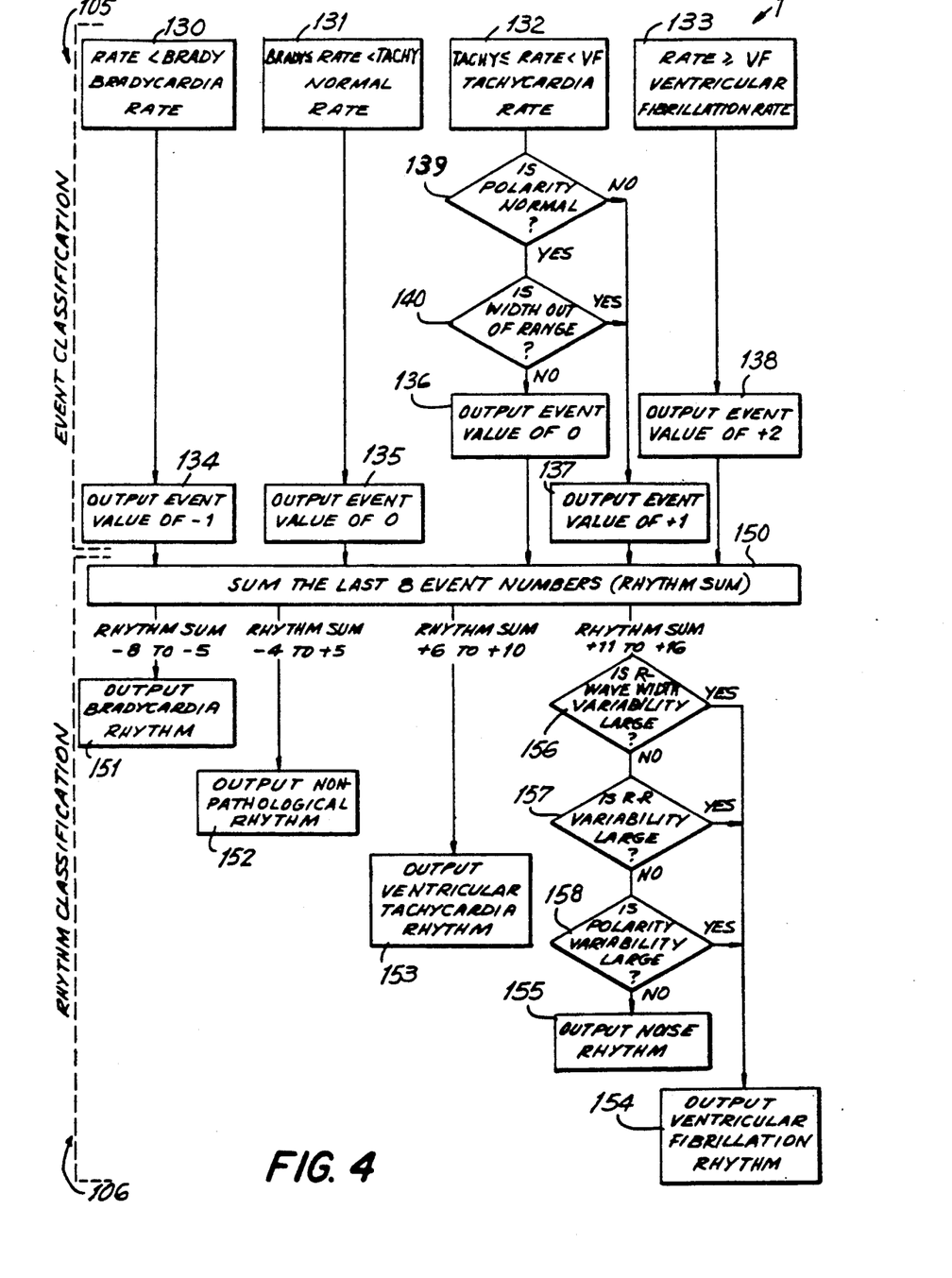
FIG. 4 is a logic flow diagram showing in greater detail a breakdown of those flow blocks of FIG. 2 that are labeled "EVENT CLASSIFICATION" and "RHYTHM CLASSIFICATION"

Referring to FIG. 4 in conjunction with FIG. 2, a logic flow diagram is presented in FIG. 4 which shows in greater detail a breakdown of the flow blocks 105 and 106 of FIG. 2, relating respectively to the event classification portion and to the rhythm classification portion of the single chamber algorithm. As shown at 130, 131, 132 and 133, the event classification portion 105 of the algorithm first separates each event into four arbitrarily assigned rate classes, including the following: (i) a bradycardia rate; (ii) a normal rate; (iii) a tachycardia rate; and, (iv) a ventricular fibrillation rate. The variables "BRADY", "TACHY" and "VF", shown in the blocks 130–133, are global initialization variables that are programmable and set by the user/clinician.

The output of the event classification portion 105 of the algorithm is an event weight or value ranging from −1 to +2, as shown at 134, 135, 136, 137 and 138. The event weights are distributed according to the following table:

−1 = a potential bradycardia beat;
  0 = a potential non-pathological beat;
  +1 = a potential ventricular tachycardia beat; and,
  +2 = a potential ventricular fibrillation beat.

As may be seen in FIG. 4, when the event rate is in the tachycardia range of block 132, the algorithm makes distinctions between intact normal conduction beats and ectopic beats based on morphological criteria. If the polarity is different from a normal beat, as shown at 139, or if the R-wave width is significantly different (e.g., more than 30% different) from that of a normal beat, as shown at 140, then the event is classified as a potential VT beat and given an output event value (weight) of +1, as shown at 137. If it is not a potential VT beat, then it is assumed to be a potential supraventricular tachycardia (SVT) beat and it is put in the potential non-pathological beat category and given an output event value (weight) of 0, as shown at 136.

In the rhythm classification portion 106 of the algorithm the event classification output values or weights for the last eight events are summed, as shown at 150, and classified into the following output rhythm categories:

| RHYTHM SUM | OUTPUT RHYTHM CATEGORY |
| --- | --- |
| −8 to −5 | Bradycardia (shown at 151) |
| −4 to +5 | Non-Pathological (shown at 152) |
| +6 to +10 | Ventricular Tachycardia (shown at 153) |
| +11 to +16 | Ventricular Fibrillation (shown at 154) |
| +11 to +16 | Noise (shown at 155) |

Ventricular fibrillation and noise, for example fan motors and other electromagnetic interference (EMI), both of which have rhythm sums in the range of +11 to +16, as indicated above, are distinguished from one another in the algorithm based on the variability of R-wave width, R-R interval and polarity, as shown in FIG. 4 at 156, 157 and 158, respectively. In the case of EMI noise, which occurs very regularly, there is very little variation in R-wave width, R-R interval and polarity of the signal being sensed. Accordingly, the algorithm determines that such variations are not large, and its rhythm classification portion outputs noise rhythm at 155 in order to avoid unnecessarily shocking the patient.

It is also noted that, aside from noise, which is separately provided for, the various rhythm sums and rhythm categories are non-overlapping and mutually exclusive from one another, so that there is no doubt of the rhythm category being outputted at any given time.

The summing of the last eight output values, which takes place at block 150, is preferably done by a buffer (not shown) of the "first-in/first-out" type which is constantly being updated, so that the sum of the latest eight events is always present. This allows the rhythm sum output to change rapidly to reflect changes in the ventricular input signal being sensed. For example, with the onset of a ventricular tachycardia rate, a ventricular tachycardia output rhythm would appear at block 154 within about two seconds, if the buffer had previously had a sum of zero (for a normal heart beat rate) in it. This would allow a safety check to be made (after the conventional five to eight seconds defibrillating capacitor charging period has expired) to determine that ventricular fibrillation still exists, before actually shocking the patient. This is of particular benefit, for example, in the case of a polymorphic VT, which may burn itself out during the capacitor charging period, returning the heart to normal sinus rhythm.

Figure 5:
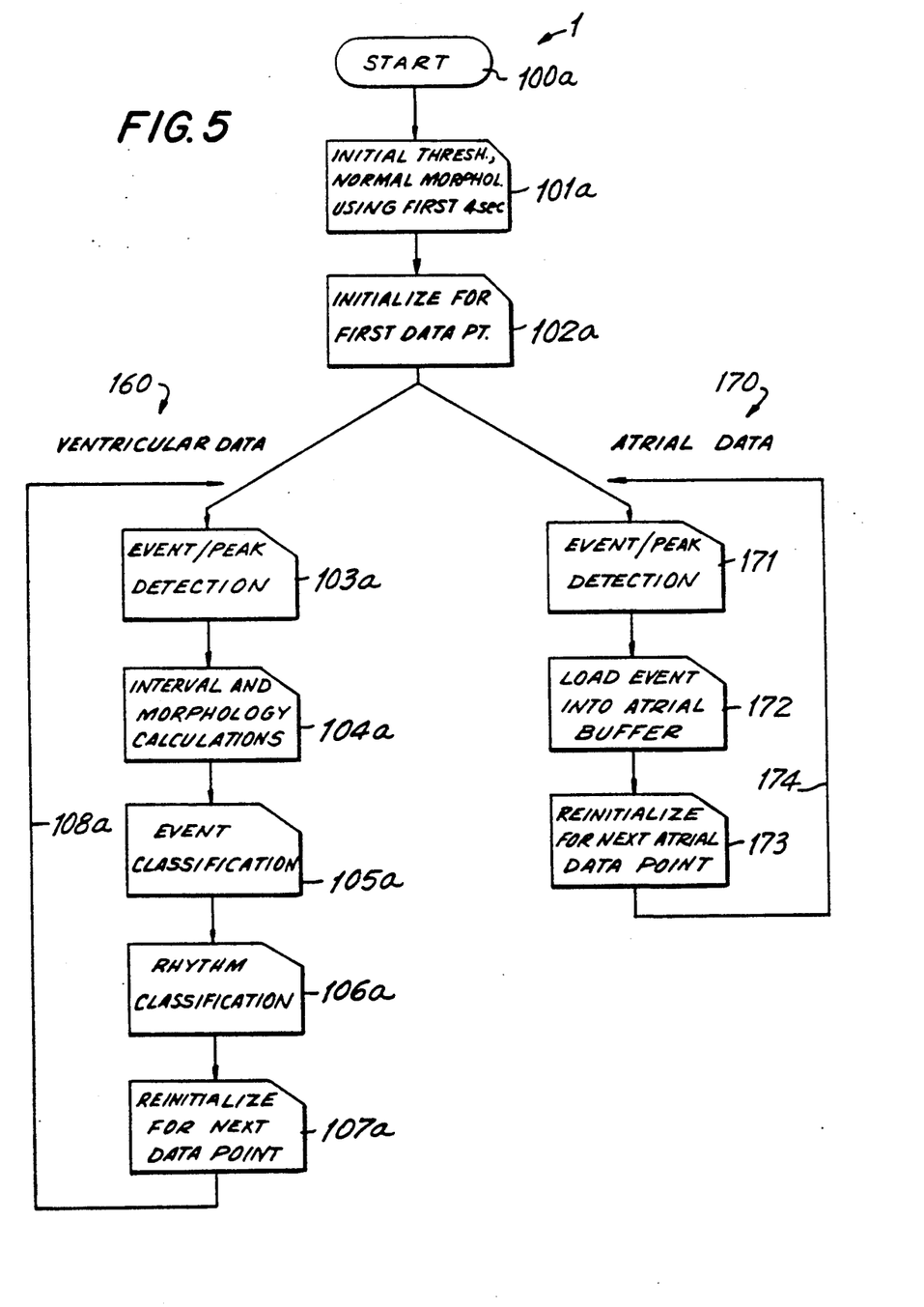
FIG. 5 is a generalized flow diagram of an arrhythmia recognition algorithm for the dual chamber type of arrhythmia control device illustrated in FIG. 1.
Figure 6:
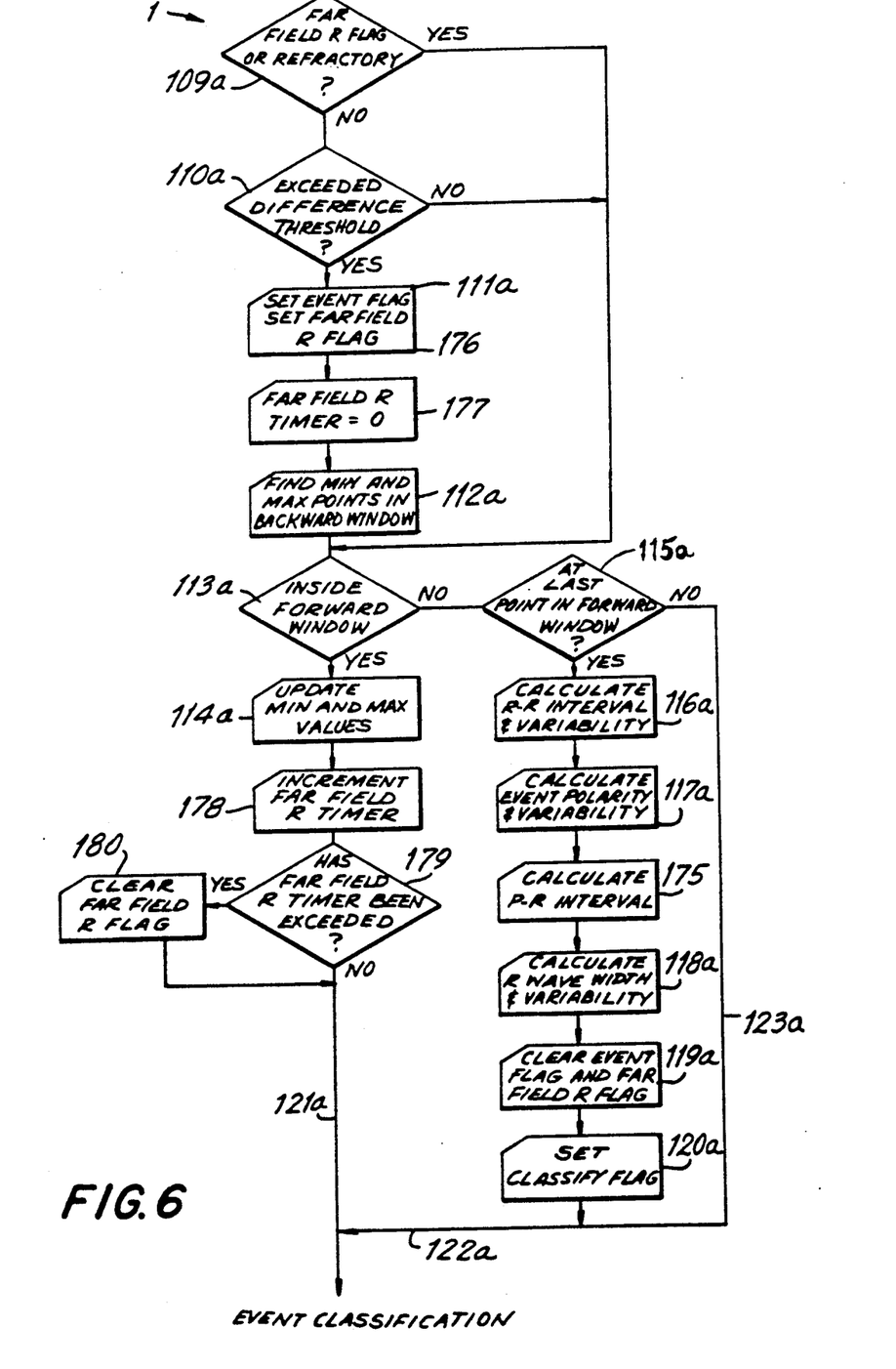
FIG. 6 is a logic flow diagram showing in greater detail a breakdown of those flow blocks of FIG. 5 that are labeled "EVENT/PEAK DETECTION" and "INTERVAL AND MORPHOLOGY CALCULATIONS"; and, FIG. 7 is a logic flow diagram showing in greater detail a breakdown of those flow blocks of FIG. 5 that are labeled "EVENT CLASSIFICATION" and "RHYTHM CLASSIFICATION".
Figure 7:
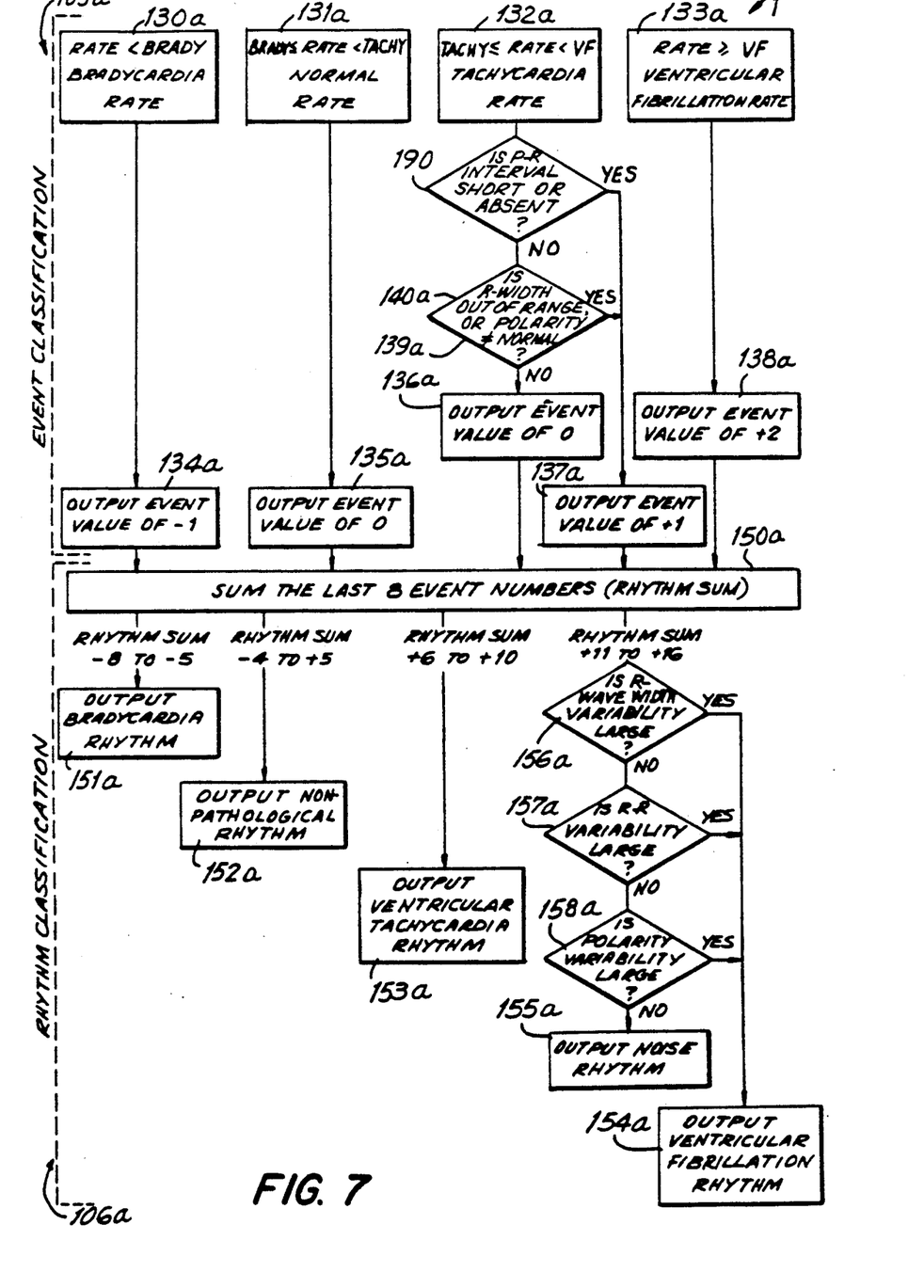

Referring now to FIG. 5, a generalized flow diagram of an arrhythmia recognition algorithm for an implantable dual chamber arrhythmia control device has there been illustrated. The arrhythmia recognition algorithm for the dual chamber device is generally similar to that of the single chamber device except that it includes additional features which take advantage of atrial data received from the atrial sensing and pacing leads 12 (FIG. 1). Accordingly, corresponding portions of the two algorithms have been assigned the same numerical designations, except that in the case of the dual chamber algorithm, which is illustrated in FIGS. 5, 6 and 7, the corresponding numerical designations each include an "a" at the end thereof.

In the dual chamber algorithm the flow is essentially the same as in the single chamber algorithm through the start-up and initialization portions of the algorithm. Thus, the starting point of the dual chamber algorithm is shown at 100a. Upon start-up of the dual chamber version of the device 1, the algorithm proceeds through a four second initialization step, shown at 101a, and then the algorithm is initialized to start viewing data for rhythm analysis, as shown at 102a.

At this point, since two input electrogram data sets are now being analyzed, there are separate flow paths, one for ventricular data, shown generally at 160, and one for atrial data, shown generally at 170. Although details of the logic differ somewhat, as will be brought out below, the general description for the ventricular data path is similar to that for the single chamber algorithm, described earlier. Thus, the ventricular path 160 of the algorithm proceeds sequentially through its event and peak detection step 103a, its interval and morphology calculations step 104a, its event classification step 105a, its rhythm classification step 106a, its reinitialization step 107a, and then loops back at 108a to the event and peak detection step 103a.

The atrial data path 170 of the algorithm, on the other hand, performs an event and peak detection determination at 171 and then loads the time of the atrial P-wave peak into an atrial buffer at 172. A count of the number of atrial events is also maintained. This information is used in the determination of intact atrial-to-ventricle (A-V) conduction and in the calculation of the P-wave to R-wave (P-R) interval. After the atrial buffer is loaded at 172, the data portion of the algorithm is reinitialized to receive the next atrial data point, at 173, and thus the flow diagram loops back to block 171, as shown at 174.

Referring to FIG. 6 in conjunction with FIG. 5, a logic flow diagram is presented in FIG. 6 which shows in greater detail a breakdown of the flow blocks 103a and 104a of FIG. 5, relating respectively to the event and peak detection and to the interval and morphology calculations portions of the algorithm. Two major differences exist between this portion of the dual chamber algorithm and the corresponding portion of the single chamber algorithm. The first major difference is that a P-R interval is calculated, as shown at 175. Upon the presence of an R-wave in the ventricular channel, the atrial event buffer 172 is searched to determine if an atrial event occurred in a P-R range such that normal or first degree heart block could be present.

The second major difference is that, in addition to an event flag being set at 111a, a far-field R-wave flag 176 is also set, and a far-field R-wave timer 177 is reset to zero. The far-field R-wave flag 176 and timer 177, which are actuated via the ventricular data channel, cause a blanking period to occur in the atrial data channel to prevent any events from being detected in that channel during the blanking period. This is done in order to prevent an atrial event from being logged during the time period when a ventricular R-wave signal is occurring, since this event might be erroneously sensed in the atrial channel as a P-wave. The far-field R-wave timer is regularly incremented, as shown at 178, and the algorithm checks to determine whether the far-field R-wave timer has completed its timing period, as shown at 179. When this timing period is completed, the far-field R-wave flag is cleared, as shown at 180.

It should be noted that the logic block 109a, in addition to checking whether the algorithm is in refractory, as in the case of the single chamber algorithm, also makes a determination as to whether or not a far-field flag has previously been set. It is also noted that event and peak detection in the atrial channel (not separately illustrated) is essentially the same as in the ventricular channel, except that no morphology calculations are performed on the atrial data.

Referring to FIG. 7 in conjunction with FIGS. 4 and 5, a logic flow diagram is presented in FIG. 7 which shows in greater detail a breakdown of respectively to the event classification portion and to the rhythm classification portion of the dual chamber algorithm. The rhythm classification portion 106a of the dual chamber algorithm is the same as the rhythm classification portion 106 (FIG. 4) of the single chamber algorithm. However, the event classification portion 105a of the dual chamber algorithm differs from the event classification portion 105 (FIG. 4) of the single chamber algorithm in that it includes an extra test for discriminating between ventricular tachycardia (VT) and supraventricular tachycardia (SVT).

Thus, the dual chamber algorithm event classification portion 105a includes an inquiry block 190 wherein the interval between the P-wave and the R-wave is determined and if that interval is found to be less than 60 milliseconds, or is found to be absent, then an event value of +1 is output, as shown at 137a, indicating an ectopic (and thus a potential VT) beat. In addition, it is noted that in the dual chamber algorithm the R-wave width inquiry block 140a is combined with the check for normalcy of polarity of the R-wave, shown at 139a. If both are normal, an event value of zero is output, as shown at 136a; if either is not normal, an event value of +1 is output, as shown at 137a.

As is apparent from the foregoing description, the present invention provides an improved arrhythmia control device that may be configured as either a single chamber or dual chamber implantable device, or may be configured to include both arrangements and allow selective switching between the two. The method of the present invention is applicable in its broader aspects not only to implantable devices but may also be used in connection with externally located cardioverters.

The dual chamber version of the device is especially effective because it is not only capable of performing the tasks of the single chamber version but it has the added benefit of being able to operate with even greater precision due to the fact that, in effect, it has "stereoscopic" vision (i.e., it looks at both the atrial waveform and the ventricular waveform at the same time), as distinguished from the "mono-vision" of the single chamber version (which sees only the ventricular waveform).

The importance of the dual chamber device is that it looks at the sequence of activation. What is expected under a normal sinus rhythm type of beat is to get activation of the atrium followed by activation of the ventricle. If the dual chamber device sees A-V synchrony, it interprets this as a normal type of beat, even if it is rather fast. On the other hand, if it detects a rapid rate in the ventricle, and the atrial beat rate is completely out of synchronization with the ventricular beat rate, the device immediately detects this and determines it to be a ventricular tachycardia situation.

The sensing electrodes 11 (FIG. 1) are preferably bipolar electrodes, as indicated earlier. The use of bipolar electrodes allows a greater amount of wave polarity information to be determined by the algorithm in both the single chamber device and the dual chamber device. The reason for this, of course, is that the polarization of the wave sensed by a conventional bipolar electrode depends on the direction from which the wave approaches the electrode. The use of this polarization information gives the algorithm additional detailed discriminatory capability in connection with event classification.

It will thus be seen from the foregoing description that the arrhythmia control system of the present invention accomplishes real time classifying of individual events in the EGM as potential bradycardia beats, normal beats, ventricular tachycardia beats or ventricular fibrillation beats, and real time classifying of the rhythm present into one of five categories: bradycardia, non-pathological, ventricular tachycardia, ventricular fibrillation or asystole; and, that these rhythms are updated on each event, or after a time-out in the case of asystole. It will also be seen that the system discriminates supraventricular tachycardia from ventricular tachycardia by using the polarity of events, as compared to normal sinus rhythm event polarity; R-wave width, as compared to normal sinus rhythm event polarity; R-wave to R-wave interval; and, in the case of the dual chamber device, P-wave to R-wave sequence of activation time. In addition, it will still further be seen that the system discriminates ventricular fibrillation from noise by using R-wave to R-wave rate variability, R-wave polarity variability, and R-wave width variability.

It should be further noted that the algorithms of the present invention act as fast as the heart rate. The faster the heart beats, the faster data is put into the event detector and the faster the rhythm classification section outputs a corresponding rhythm. Thus, the algorithms provide for rapid detection of tachycardia, and even faster fibrillation detection. This correlates with the needs of the patient.

In addition, it is noted that various safety factors are built into the algorithms to insure that they do not miss any important activity occurring in the patient's heart. By checking various factors (e.g., beat rate, R-wave width, interval and polarity, and their variabilities, noise, and atrial data in the case of the dual chamber algorithm) and summing (or averaging) the event classification outputs in the rhythm classification buffer, the algorithm prevents hasty and inappropriate action from being taken by the arrhythmia control device.

It will be apparent to those skilled in the art that numerous software programs in various codes may be devised to implement the single chamber and dual chamber algorithms of the present invention and, therefore, it is not intended that this invention be limited to the use of any specific software programs.

Although the invention has been described with reference to particular embodiments, it is to be understood that such embodiments are merely illustrative of the application of the principles of the invention and that various other changes can be made. For example, the event data windows that are established when event peaks are detected may extend solely backward in time or solely forward in time of the trigger point, rather than in both directions from that point. Also, the delivery of electrical therapy following the detection of a tachyarrhythmia may be immediate, or it may be dependent on the charge time of a capacitor. Alternatively, the time to the delivery of therapy may depend on the haemodynamic condition of the patient. In this regard, reference is made to the U.S. Pat. No. 4,895,151 of Lorraine Holley and Richard Grevis, entitled "Apparatus And Method For Therapy Adjustment In Implantable Cardioverter", which is incorporated herein by reference. Numerous other modifications may be made and other arrangements may be devised without departing from the spirit and scope of the present invention.

I claim:

1. A cardioverting device for reverting tachycardia in a patient's heart, said device including means for sensing the ventricular waveform of the heart, means for storing data corresponding to said waveform, and means for delivering cardioversion shock therapy to the heart, said device further comprising:

means for detecting event peaks in said waveform and establishing event data windows extending for predetermined time periods relative to each of said event peaks;

means responsive to the detection of an event peak in said waveform for determining the morphology of that portion of said waveform which occurs within said event data window;

means for classifying each of said events based on said morphology, said means outputting in real time at least one of a plurality of different values corresponding to at least one of a plurality of different heart rate categories, including at least a normal rate, a tachycardia rate and a ventricular fibrillation rate;

means for summing the output of said event classifying means during a predetermined number of events, said means outputting in real time at least one of a plurality of different rhythm signals based on said summing and corresponding at least to a non-pathological rhythm, a pathological ventricular tachycardia rhythm and a pathological ventricular fibrillation rhythm; and, means responsive to said output summing means for delivering appropriate therapy to the heart when said rhythm signal corresponds to one of said pathological rhythms.

2. A device according to claim 1, further including means for providing antitachycardia pacing to said heart.

3. A device according to claim 2, further including means for providing bradycardia support pacing to said heart.

4. An implantable combined dual chamber pacing and cardioverting device adapted to be electrically connected to the atrium and ventricle of a patient's heart for the reversion of tachycardias, said device including means for sensing the atrial and ventricular waveforms of the heart, means for storing data relating to said waveforms, and means for delivering cardioversion shock therapy to the heart, said device further comprising:

means for detecting event peaks in said ventricular waveform and establishing event data windows extending for predetermined time periods relative to each of said event peaks;

means responsive to the detection of an event peak in said waveform for determining the morphology of that portion of said ventricular waveform which occurs within said event data window;

means for classifying each of said events based on said morphology, said means outputting in real time at least one of a plurality of different values corresponding to at least one of a plurality of different heart rate categories, including at least a normal rate, a tachycardia rate and a ventricular fibrillation rate;

means for summing the outputs of said event classifying means during a predetermined number of events, said means outputting in real time at least one of a plurality of different rhythm signals based on said summing and corresponding to nonpathological rhythm, a pathological ventricular tachycardia rhythm and a pathological ventricular fibrillation rhythm; and means responsive to said output summing means for delivering appropriate therapy to the heart when said rhythm signal corresponds to one of said pathological rhythms.

5. An implantable combined dual chamber pacing and cardioverting device adapted to be electrically connected to the atrium and ventricle of a patient's heart for the reversion of tachycardias, said device including means for sensing the atrial and ventricular waveforms of the heart, means for storing data relating to said waveforms, and means for delivering cardioversion shock therapy to the heart, said device further comprising:

means for detecting event peaks in said ventricular waveform and establishing event data windows extending for predetermined time periods relative to each of said event peaks;

means responsive to the detection of an event peak in said waveform for determining the morphology of that portion of said ventricular waveform which occurs within said event data window;

means for classifying each of said events based on said morphology, said means outputting in real time at least one of a plurality of different values corresponding to at least one of a plurality of different heart rate categories, including at least a normal rate, a tachycardia rate and a ventricular fibrillation rate;

means for summing the outputs of said event classifying means during a predetermined number of events, said means outputting in real time at least one of a plurality of different rhythm signals based on said summing and corresponding to a non-pathological rhythm, a pathological ventricular tachycardia rhythm and a pathological ventricular fibrillation rhythm; and, means responsive to said output summing means for delivering appropriate therapy to the heart when said rhythm signal corresponds to one of said pathological rhythms.

6. A device according to claim 5, further including means for providing bradycardia support pacing to both the atrium and the ventricle.

7. A device according to any one of claims 1 and 4-6, wherein said device includes a microprocessor having a pulse clock timing mechanism therein, wherein said event data windows extend on opposite sides of and for predetermined time periods both before and after each of said event peaks, wherein said predetermined time period of the portion of said event data window occurring after said event peak is about fifty percent longer than said predetermined time period of the portion of said event data window occurring before said event peak, and wherein said predetermined time periods are timed by said pulse clock timing mechanism.

8. A device according to any one of claims 1 and 4–7, wherein said morphology determining means determines the widths and polarities of the R-waves of the heart, and the intervals between such R-waves.

9. A device according to claim 8, wherein said event classifying means utilizes said R-wave width, polarity and interval information to distinguish between ventricular fibrillation signals and noise signals occurring in the ventricular waveform.

10. A device according to anyone of claims 1 and 4–6, wherein the range of values required to be summed by said summing means during said predetermined number of events to output each of said rhythm signals is different from and non-overlapping with the range of values required to be summed during said predetermined number of events for the others of said rhythm signals.

11. A device according to any one of claims 5–6, wherein said morphology determining means determines the widths and polarities of the R-waves of the heart, the intervals between such R-waves, and the intervals between the P-waves of the heart and the R-waves of the heart.

12. A device according to claim 11, wherein said event classifying means utilizes the information with respect to the interval between the P-wave and the R-wave to distinguish between ventricular tachycardia and supraventricular tachycardia.

13. A device according to claim 12, wherein said event classifying means utilizes said R-wave width, polarity and interval information to distinguish between ventricular fibrillation signals and noise signals occurring in the ventricular waveform.

14. A device according to claim 12, wherein said means for classifying each of the events based on morphology also outputs a value corresponding to a bradycardia rate.

15. A device according to claim 14, wherein said means for summing the outputs of said event classifying means also outputs a rhythm signal based on said summing which corresponds to a bradycardia rate.

16. A device according to claim 12, wherein said means for classifying each of the events based on morphology also outputs a value corresponding to a bradycardia rate.

17. A device according to claim 16, wherein said means for summing the outputs of said event classifying means also outputs a rhythm signal based on said summing which corresponds to a bradycardia rate.

18. A method of reverting tachycardia in the heart of a patient, comprising the following steps:
    sensing the ventricular waveform of the heart;
    storing data corresponding to said ventricular waveform;
    detecting event peaks in said ventricular waveform and establishing event data windows extending for predetermined time periods with respect to each of said event peaks;
    in response to the detection of an event peak in said waveform, determining the morphology of that portion of said ventricular waveform which occurs within said event data window;
    classifying each of said events based on said morphology and providing in real time a plurality of different rate signals corresponding to at least one of a plurality of different heart rate categories, including at least a normal rate, a tachycardia rate and a ventricular fibrillation rate;
    summing said rate signals during a predetermined number of events and providing in real time at least one of a plurality of different rhythm signals based on said summing and corresponding at least to a non-pathological rhythm, a pathological ventricular tachycardia rhythm and a pathological ventricular fibrillation rhythm; and
    delivering appropriate electrical shock therapy to the heart when said rhythm signal corresponds to one of said pathological signals.

19. A method according to claim 18, wherein each of said event data windows extends for a predetermined time period both before and after each of said event peaks.

20. A method according to claim 19, wherein the electrical shock therapy is delivered to the ventricle.

21. A method according to claim 20, wherein during the step of determining the morphology of the ventricular waveform, the widths and polarities of the the R-waves of the heart, and the intervals between said such R-waves, are determined.

22. A method according to claim 18, including the steps of sensing the atrial waveform of the patient's heart and storing data corresponding to said atrial waveform.

23. A method according to claim 22, wherein each of said event data windows extends for a predetermined time period both before and after each of said event peaks.

24. A method according to claim 23, wherein the electrical shock therapy is delivered to both the atrium and the ventricle.

25. A method according to claim 24, wherein during the step of determining the morphology of the ventricular waveform, the widths and polarities of the R-waves of the heart, the intervals between said R-waves, and the intervals between the P-waves and the R-waves of the heart are determined.

26. A method according to any one of claims 21 and 25, wherein during the step of classifying each of the events based on morphology, said R-wave width, polarity and interval information is utilized to distinguish between ventricular fibrillation signals and noise signals occurring in said ventricular waveform.

27. A method according to claim 25, wherein during the step of classifying each of the events based on morphology, said information with respect to the interval between the P-wave and the R-wave of the patient's heart is utilized to distinguish between ventricular tachycardia and supraventricular tachycardia.

28. A method according to claim 27, wherein during the step of classifying each of the events based on morphology, said R-wave width, polarity and interval information is utilized to distinguish between ventricular fibrillation signals and noise signals occurring in said ventricular waveform.

29. A method according to any one of claims 18–25, 27 and 28, wherein during the step of providing a plurality of different rate signals corresponding to different heart rate categories, a rate signal corresponding to a bradycardia rate is also provided.

30. A method according to claim 29, wherein during said step of providing a plurality of different rhythm signals based on the summing of said rate signals, a rhythm signal corresponding to a bradycardia rhythm is also provided.

31. A method according to any one of claims 18-25, 27 and 28, wherein the range of rate signals required to be summed during said predetermined number of events to provide each of said rhythm signals is different from and non-overlapping with the range of rate signals required to be summed during said predetermined number of events for the others of said rhythm signals.

* * * * *